May 13, 1969 E. S. BOERNER Plant Pat. 2,886
ROSE PLANT
Filed Oct. 13, 1967
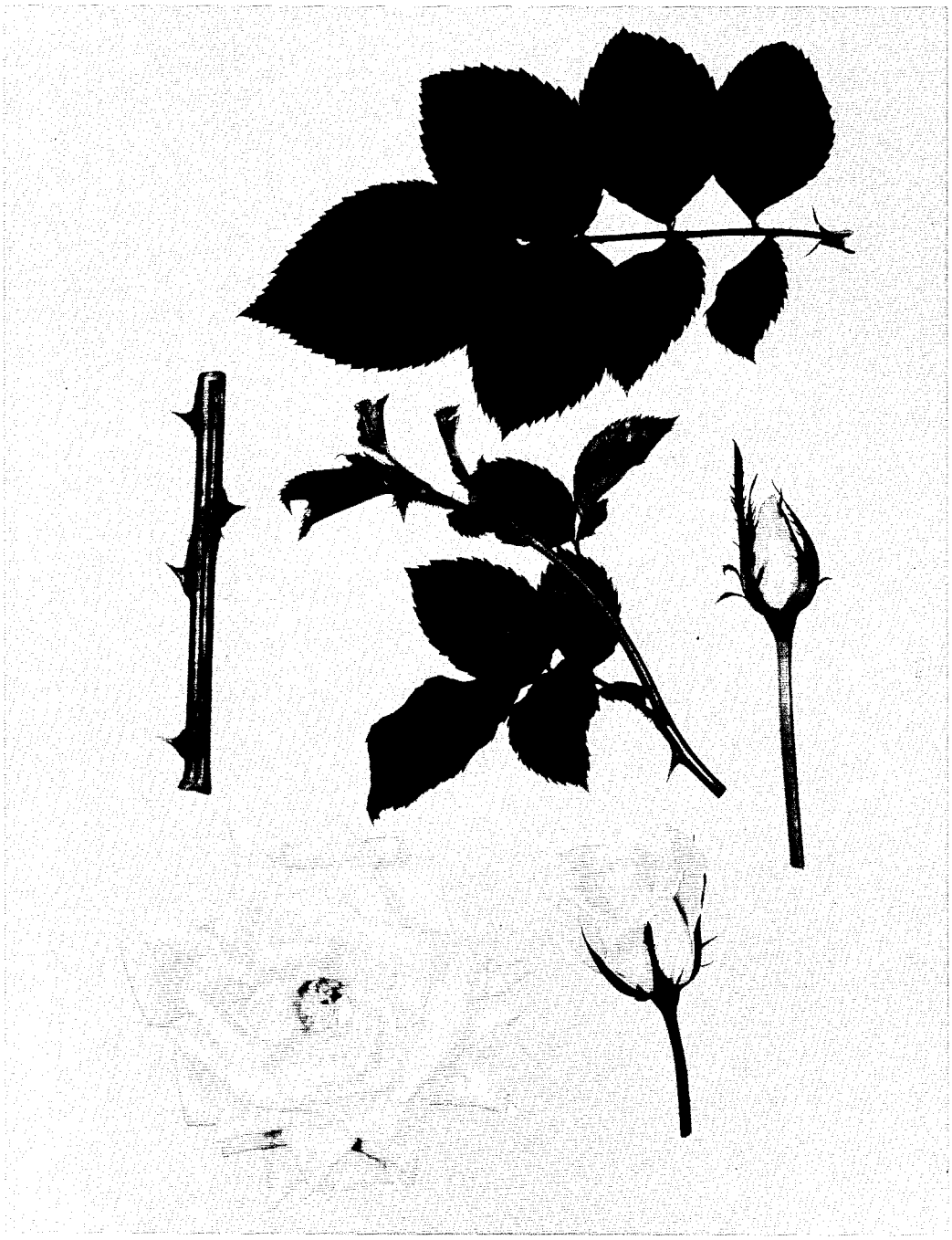
E. S. Boerner, Inventor.
Deceased
By: Lincoln Rochester Trust Company
By: Edward L. Jenner, Trust Officer
and Roger L. Boerner,
Executors
By: Robb & Robb, Attorneys.

United States Patent Office

Plant Pat. 2,886
Patented May 13, 1969

2,886
ROSE PLANT

Eugene S. Boerner, deceased, late of Benton, N.Y., by Lincoln Rochester Trust Company, Rochester, N.Y., and Roger L. Boerner, Milwaukee, Wis., executors, assignors to Jackson & Perkins Company, Newark, N.Y., a corporation of New York

Filed Oct. 13, 1967, Ser. No. 675,718
Int. Cl. A01h *5/02*
U.S. Cl. Plt.—26 1 Claim

The present invention relates to a new and distinct variety of rose plant of the floribunda class, which was originated by the late Eugene S. Boerner, deceased, by crossing an unnamed and unpatented seedling derived from a cross of the rose variety known as "Fashion" (Plant Patent No. 789) × the rose variety known as "Hawaii" (Plant Patent No. 1,833) with the rose variety known as "Zorina" (Plant Patent No. 2,321).

The primary objective of this breeding was to produce a new and improved floribunda rose variety suitable for use both as a garden variety and a greenhouse cut-flower variety. This objective was fully achieved, along with other desirable features, as evidenced by the following unique combination of characteristics which are outstanding in the new variety and which distinguish it from its parents, as well as from all other varieties:

(1) An upright habit of plant growth suitable for garden use;

(2) Excellent suitability as a greenhouse variety having a high cut-flower productivity;

(3) Abundant foliage having a distinctive and attractive Hay's Maroon color;

(4) An attractive ovoid pointed flower bud form; and (5) A distinctive and attractive flower color corresponding to Thulite Pink, overcast with Cameo Pink.

Asexual reproduction of the new variety by budding, as performed at Newark, N.Y., and also at Pleasanton, Calif., shows that the aforementioned characteristics and distinctions come true to form and are established and transmited through succeeding propagations.

The accompanying drawing shows typical specimens of the vegatative growth and flowers of the new variety in different stages of development and as depicted in color as nearly true as it is reasonably possible to make the same in a color illustration of this character.

The following is a detailed description of the new rose variety, with color terminology in accordance with Ridgway's Color Standards and Nomenclature:

Parentage: Seedling.

*Seed parent.*—An unnamed seedling of "Fashion" × "Hawaii."

*Pollen parent.*—"Zorina."

Classification:

*Botanic.*—Floribunda.

*Commercial.*—Floribunda.

Propagation: Holds its distinguishing characteristics through succeeding propagations by budding.

*Flower*

(Observations made from specimens grown in a greenhouse at Newark, N.Y. in the early morning late in the month of August.)

Blooming Habit: Recurrent—continuous, with high cut-flower productivity in greenhouse.

Bud:

*Size.*—Medium.

*Form.*—Ovoid pointed; is not affected by wet or hot weather.

*Color.*—When sepals first divide—Straw Yellow, Plate 16. When petals begin to unfurl—Flesh Color, Plate 14, lightly overcast with Eugenia Red, Plate 13, on the outer edge of the petal. When half-blown: inside of petals—Thulite Pink, Plate 26; reverse of petals—Thulite Pink, Plate 26, lightly overcast with Hermosa Pink, Plate 1 and with the lower half of the petal Pale Ochraceous-Buff, Plate 15.

*Sepals.*—Branched; curl back when petals begin to unfurl. Color: inside—Turtle Green, Plate 32; outside—Parrott Green, Plate 6.

*Calyx.*—Color—Parrott Green, Plate 6. Shape—funnel. Size—small. Aspect—smooth. Odor when rubbed—none.

*Peduncle.*—Length — medium. Aspect — smooth. Strength—erect; slender. Color—Light Elm Green, Plate 17.

*Opening.*—Opens up well; is not affected by adverse weather conditions.

Bloom:

*Size.*—Medium. Average size when fully expanded—from 3 inches to 3¼ inches.

*Borne.*—Both singly and several together.

*Stems.*—Medium length; strong.

*Form (when first open).*—High-centered. Permanence—retains its form to the end, but outer petals curl back.

*Petalage.*—Double (full but open center). Number of petals under normal conditions—from 30 to 35.

*Color.*—Center of flower—Thulite Pink, Plate 26, lightly overcast with La France Pink, Plate 1. Outer petals—Thulite Pink, Plate 26. Base of petals (aiglets)—Apricot Yellow, Plate 4. Inside of petals—Thulite Pink, Plate 26, overcast with Cameo Pink, Plate 26. Reverse of petals—Ivory Yellow, Plate 30, with outer edge of petal very lightly overcast with La France Pink, Plate 1. General tonality from a distance—Thulite Pink, Plate 26, overcast with Cameo Pink, Plate 26.

*Discoloration.*—General tonality at end of first day—Thulite Pink, Plate 26, lightly overcast with La France Pink, Plate 1. Second day—Thulite Pink, Plate 26, overcast with Cameo Pink, Plate 26. Third day—Thulite Pink, Plate 26, overcast with Cameo Pink, Plate 26.

Petals:

*Texture.*—Leathery; is not affected by wet or hot weather.

*Appearance.*—Inside—satiny. Outside—shiny.

*Form.*—Oval; slightly notched.

*Arrangement.*—Imbricated (regularly arranged shingle-like).

*Petaloids in center.*—Few; small.

*Persistence.*—Drop off cleanly.

*Fragrance.*—Strong. Nature—tea (average hybrid tea scent).

*Lasting quality.*—On the plant—very long. As cut flower—very long.

*Genital organs*

Stamens, anthers: Medium size; many; regularly arranged around styles. Color—Light Orange-Yellow, Plate 3.

Stamens, filaments (threads): Medium length. Color—Baryta Yellow, Plate 4.

Pollen: Color—Pinard Yellow, Plate 4.

Styles: Bunched; uneven length; short; thin.

Stigmas: Color—Naples Yellow, Plate 16.

Ovaries: All enclosed in calyx.

Hips: None.

Seeds: None.

*Plant*

Form: Bush.

Growth: Vigorous; upright.

Foliage: Compound of 3–7 leaflets.

*Size.*—Large.

*Quantity.*—Abundant.

*Color.*—New foliage: upper side—Hay's Maroon, Plate 13; underside—Van Dyke Red, Plate 13. Old foliage: upper side—Dark Cress Green, Plate 31; under side—Light Elm Green, Plate 17.

*Shape.*—Oval pointed.

*Texture.*—Upper side—glossy. Under side—smooth.

*Ribs and veins.*—Ordinary.

*Edge.*—Serrated (saw toothed).

*Serration.*—Single; small

*Leaf stem.*—Color—Rainette Green, Plate 31. Under side—prickly.

*Stipules.*—Medium length; bearded.

Wood:

*New wood.*—Color—Yellowish-Olive, Plate 30. Bark—smooth.

*Old wood.*—Color—Light Hellebore Green, Plate 17. Bark—smooth.

Thorns:

*Thorns.*—Quantity: on main stalks from base—ordinary; on laterals from stalk—ordinary. Form— narrow base; medium length; hooked downward. Color (when young)—Bordeaux, Plate 12. Position—irregular.

*Prickles.*—Quantity: on main stalks—none; on laterals—none.

*Short needles.*—Quantity: on main stalks—none; on laterals—none.

What is claimed is:

1. A new and distinct variety of rose plant of the floribunda class, substantially as herein shown and described, characterized particularly as to novelty by the unique combination of an upright habit of plant growth suitable for garden use, excellent suitability as a greenhouse variety having a high cut-flower productivity, abundant foliage having a distinctive and attractive Hay's Maroon color, an attractive ovid pointed flower bud form and a distinctive and attractive flower color corresponding to Thulite Pink, overcast with Cameo Pink.

No References Cited.

ROBERT E. BAGWILL, *Primary Examiner.*